United States Patent [19]

Cornieri et al.

[11] Patent Number: 5,130,061
[45] Date of Patent: Jul. 14, 1992

[54] PROCESS FOR THE EXTRACTION OF POLYUNSATURATED FATTY ACID ESTERS FROM FISH OILS

[75] Inventors: Franco Cornieri; Walter Di Fulvio, both of Florence, Italy

[73] Assignee: Innova di Ridolfi Flora & C. s.a.s., Florence, Italy

[21] Appl. No.: 357,650

[22] Filed: May 24, 1989

Related U.S. Application Data

[63] Continuation-in-part of Ser. No. 199,306, May 26, 1988, abandoned.

[30] Foreign Application Priority Data

May 28, 1987 [IT] Italy .................. 20700 A/87

[51] Int. Cl.$^5$ .............................................. C09F 5/10
[52] U.S. Cl. ............................. 554/167; 424/523; 554/175; 554/193; 554/206; 554/210; 554/224
[58] Field of Search ............... 424/523; 260/412, 413, 260/419, 420, 421, 423, 424, 425, 426, 427, 428, 428.5

[56] References Cited

U.S. PATENT DOCUMENTS

| | | | |
|---|---|---|---|
| 4,164,506 | 8/1979 | Kawahara et al. | 260/421 |
| 4,179,454 | 12/1979 | Mehta et al. | 260/419 |
| 4,377,526 | 3/1983 | Fujita et al. | 260/424 |
| 4,438,106 | 3/1984 | Wagu et al. | 514/58 |
| 4,526,902 | 7/1985 | Rubin | 514/560 |
| 4,554,107 | 11/1985 | Takao | 260/421 |
| 4,675,132 | 6/1987 | Stout et al. | 260/410.9 R |
| 4,792,418 | 12/1988 | Rubin et al. | 260/420 |

Primary Examiner—Douglas W. Robinson
Assistant Examiner—Jean C. Witz
Attorney, Agent, or Firm—Walter H. Schneider

[57] ABSTRACT

A process for the extraction of eicosapentaenoic (EPA) and docosahexaenoic (DHA) acid esters from crude fish oils, by means of transesterification with ethanol and $H_2SO_4$ and two-step molecular distillation.

2 Claims, No Drawings

PROCESS FOR THE EXTRACTION OF POLYUNSATURATED FATTY ACID ESTERS FROM FISH OILS

This application is a continuation-in-part of application Ser. No. 199,306 filed May 26, 1988 now abandoned.

The present invention relates to a process for the preparation of a mixture of fatty acid alkyl esters having a high concentration in eicosapentaenoic and docosahexaenoic acids, starting from fish oils of various origin, and to pharmaceutical and/or dietetic compositions containing said mixture.

Moreover, the process according to the invention is suited to deodorize and deacidify said oils, in view of any dietetic and/or alimentary use.

Polyunsaturated fatty acids are known to play two important roles in human physiology: a structural role, as constituents of cell membrane phospholipids, and a functional role, as Prostaglandin precursors.

In fact, fatty acids of the α-linolenic acid family have a basic role in development and function of brain, retina and gonads, as well as the formation of $PGI_3$ and $TxA_3$, which are factors of paramount importance for the anti-platelet aggregating activity.

Among these, particularly important are the long chain members of the ω-3-family, i.e. eicosapentaenoic (20:5ω-3) or EPA and docosahexaenoic (22:6ω-3) or DHA acids, derivating from desaturation and elongation of α-linolenic acid, thanks to the intervention of the related enzymes (Δ-desaturase).

EPA, as the precursor of $PGI_3$ and $TxA_3$, exerts an anti-platelet aggregating activity and an anti-thrombotic effect which can be related to cyclooxygenase inhibition (aspirine-like effect) and/or to the competition with arachidonic acid for said enzyme, with an accordingly decreased synthesis of $PGI_2$ and $TxA_2$, which are known platelet aggregating agents.

DHA is the most important component of human lipids and brain and is present in high concentrations in synaptic membranes phospholipids, which may imply a role in nervous impulse transmission. Moreover, DHA being a structural element of platelet cell, it indirectly exerts an important role in anti-thrombotic action, due to the increase in platelet fluidity.

Recent studies evidenced a decrease in Δ-6 desaturase in man as the age goes on (after 35 years); said phenomenon causes thus an endogenous lack in the above mentioned acids, which therefore should be administered through diet or by means of suitable compositions. However, various practical difficulties opposed up to now a wide use of said acids in therapy or as alimentary integrators, which use on the other hand should be highly desirable, in view of the above reported biochemical and pharmacological considerations.

Said difficulties mainly relate to extraction of said acids from fish oils, purification and concentration to values convenient for the pharmaceutical use and deodorization thereof.

Even though a number of methods have already been proposed and disclosed, the above objects have still not been attained satisfactorily, as proved, inter alia, by the still restricted use of EPA and/or DHA, in spite of the remarkable potentialities thereof as drugs or alimentary integrators. The methods up to now known, which are based on different techniques such as degreasing, countercurrent extraction, urea addition, liquid chromatography, and distillation, give rather low yields and products which easily deteriorate if exposed to air or light. Moreover, the major part of the known methods refers to purification of only eicosapentaenoic acid, to the detriment of other useful unsaturated acids, such as DHA.

As an example, U.S. Pat. No. 4.377.526 discloses a process for purification of EPA or the esters thereof, which comprises treatment with urea, followed by fractional distillation. By said method, EPA percentages higher than 70% are obtained, whereas DHA is present only as a residue (3–5%).

More recently, U.S. Pat. Nos. 4.554.107 and 4.623.488 disclosed a purification method based on the technique known as molecular distillation: in this case, a deodorized fish oil is obtained which is enriched in EPA and DHA, in rather low yields (30%), due to the drastic conditions used.

A first object of the invention is therefore provided by a method for the extraction of DHA and EPA ethyl esters from crude fish oils in high yields, under conditions which can easily be applied on industrial scale, which give a stable and odourless product, which can be used in human therapy or as a dietetic and alimentary integrator.

A second object of the invention, in fact, is provided by pharmaceutical or alimentary compositions containing as the active ingredient a mixture of EPA and DHA ethyl esters, for the treatment or the prophylaxis of cardio-vascular diseases.

According to one embodiment of the present invention, it has been found that highly purified mixtures having a total EPA/DHA ethyl ester content of at least about 65% can be obtained starting from crude fish oil by subjecting the latter to transesterification with ethanol in the presence of a catalytic amount of sulfuric acid, extracting the reaction product with a hydrocarbon, e.g., cyclohexane, and then subjecting the extract to silica gel chromotography and multi-step, i.e., at least two-step, molecular distillation under controlled conditions.

According to a second embodiment of the invention, a mixture in which the DHA ethyl ester content is 85–95%, and even higher, can be obtained by dissolving the reaction product, obtained from the silica gel chromotography, in acetone accompanied by slow cooling and then subjecting the residue obtained by filtration and removal of the solvent to multi-stage molecular distillation.

The process of the invention can be easily carried out on industrial scale, and is characterized in that it consists in a surprisingly low number of steps, if compared with the processes up to now known, which use crude fish oils as the starting material. Moreover, it should be stressed as particularly surprising that enriching in EPA and DHA and deodorizing are simultaneously attained by a molecular distillation technique, which has been hitherto considered merely for the purpose of deodorization, with completely different operative parameters.

In fact, the above cited U.S. patents carry out three-steps molecular distillation on long chain unsaturated acid triglycerides, using drastic temperature conditions (up to 260°–300° C.), operating in the presence of two additives (glycerol and momooleylglyceride) in order to fluidize the liquid to be distilled.

On the contrary, the process object of the present invention is characterized in that it is carried out on the ethyl ester mixture instead of the triglycerides; moreover operative conditions are much milder (only two steps at a lower temperature) and give higher yields, mainly in DHA which is known to be less stable.

According to the invention, deodorization is effected in the first step and the products responsible for the bad smell are removed by the low temperature trap, upstream the pump. This allows to operate on crude oil not previously depurated, which, besides being effectively deodorized, is also deacidified, to make it suited for alimentary use.

A preferred EPA and DHA source consists in oils deriving from working of "blue fish", such as anchovies, sardines, cods, mackerels, herrings and the like.

The oil is diluted with ethanol, then refluxed in the presence of catalytic amounts of concentrated sulfuric acid. After extraction with hexane, the transesterification mixture is subjected to silica gel chromatography, then to a two-step molecular distillation process, with a vacuum of about $10^{-3}$ mm Hg and at an evaporation temperature ranging from 65°-70° C. to 105°-125° C. and condenser at 5° C.

The product obtained as a distillation residue has and EPA+DHA content higher than 65% and the DHA:EPA ratio, which generally depends on the starting oil, is about 3:2.

According to an alternative process of the invention, the ethanolic solution obtained by transesterification can be treated with urea, in order to remove the salts of fatty acids of lower unsaturation. However, said further step generally is not necessary, since in the major part of cases the only molecular distillation alone is sufficient to attain the desired effects.

According to a further aspect of the process of the invention, it is also possible to obtain docosahexaenoic acid having an assay as high as 85-95%, according to the starting fish oil used. For this purpose, the ester mixture from the silica gel chromatography is dissolved in acetone and the solution slowly cooled to $-40°$ C. The formed precipitate is then filtered, the solvent is removed under reduced pressure and the residue is subjected to molecular distillation, which is carried out in two steps, always at $10^{-3}$ torr, but at higher temperatures, namely 80°/100° C. for the first step and 105°/125° C. for the second step. A product having a DHA ethyl ester content greater than 95% can be obtained by subjecting a mixture having a 80-90%, or greater total content of EPA/DHA ethyl esters to further molecular distillation at a vacuum of $10^{-3}$ mm Hg and a temperature in the range of 50-110° C.

The product obtained by the process of the invention proved to be particularly convenient for pharmaceutical use, in form of appropriate pharmaceutical compositions. In fact, a favourable synergism was evidenced between EPA and DHA, such as to give a therapeutical efffectiveness higher than that of the single components. The pharmaceutical compositions of the invention will be prepared by means of techniques and excipients conventionally used for active ingredients in form of oils, as described in "Remington's Pharmaceutical Sciences handbook", Hack Pub. Co., N.Y. USA. Preferred administration routes are the oral and the parenteral ones, whereas posology will generally range form 500 to 5.000 mg of EPA and DHA ethyl ester mixture obtained by the inventive process, depending on pathology and conditions of the patient to be treated. Anyway, higher dosages are not controindicated, since the active ingredient is almost non-toxic. The same mixture can be used as dietetic or alimentary integrator, optionally diluted with other appropriate vegetal oils.

In fact, the mixture obtained by the process of the invention is particularly convenient for the prophylaxis of diseases related to platelet hyperaggregation conditions, since it is completely free from linolenic acid derivatives which are precursors of arachidonic acid and accordingly of $PGE_2$ and $TxA_2$ which are factors able to oppose and make void the favourable pharmacologic properties deriving from the production of $PGI_3$ and $TxA_3$, induced by EPA, DHA and derivatives thereof.

The following example further illustrates the invention without limiting it.

EXAMPLE 1 a) 80 kg of fish oil was dissolved in 50 l of ethanol containing 5% conc. sulfuric acid. The whole was refluxed under nitrogen for 8 hours, then cooled; ethanol excess was removed and the volume was doubled with water. At this moment an extraction was carried out with appropriate amounts of hexane. The hexane solution, after repeated washings with water, was chromatographed on a silica gel 100 column to remove impurities. The solution from this column was freed from n-hexane under vacuum, to obtain a yield of about 65 kg of esterified products. Control can be effected by G.C. (gas chromatography).

b) The product from step a) was subjected to double-step molecular distillation, under a vacuum of about $10^{-3}$ mm Hg, at an evaporation temperature of 65°-70° C. and condenser temperature of 5° C.

Percentages of the fatty acids present in the oil before and after the treatment, determined by G.C., are reported hereinbelow.

| Fatty acids | %* Ethyl esters on crude product | %* Ethyl esters on final product |
|---|---|---|
| $C_{14}: 0$ | 8.4 | 0.1 |
| $C_{16}: 0$ | 16.0 | 1.7 |
| $C_{16}: 1\omega 7$ | 9.8 | 0.3 |
| $C_{18}: 1\omega 9$ | 9.9 | 3.0 |
| $C_{18}: 1\omega 7$ | 3.1 | 1.0 |
| $C_{20}: 5\omega 3$ | 9.6 | 29.8 |
| $C_{22}: 5\omega 3$ | 1.0 | 4.1 |
| $C_{22}: 6\omega 3$ | 10.7 | 39.9 |

EXAMPLE 2

80 kg of fish oil together with 50 kg of ethanol were placed in a closed reactor containing 2.5 kg of conc. sulfuric acid and refluxed under nitrogen for six hours at a temperature of 82°±° C. Control was effected by T.L.C. on silica gel plates using a mixture of petroleum ether/diethyl ether/acetic acid (85/14/1) as the eluant. The developer comprised a 1:1 mixture of conc. sulfuric acid and methyl alcohol. When the chromatographic control showed the end of the reaction, heating was discontinued and excess ethanol removed by distillation. The residue was cooled to room temperature and added to 200 kg of water 150 kg of cyclohexane. The mixture was stirred and the water discharged. Water washings were repeated until the discharge showed a neutral reaction. The cyclohexane solution was dried with anhydrous sodium sulfate and the cyclohexane removed by vacuum distillation (20 mm Hg) at 60° C. The product residue comprising EPA and DHA ethyl esters was stored under nitrogen for subsequent molecular distillation.

EXAMPLE 3

35–40% Total Conc. Combined EPA/DHA Ethyl Esters

The product of Example 2 was subjected to molecular distillation under a pressure of $10^{-3}$ mm Hg and an evaporator temperature of 90°–110° C. to remove natural and process impurities. The purified product obtained had the EPA (15–20%) concentrations originally present in the starting fish oil of Example 2.

EXAMPLE 4

40–50% Total Conc. EPA/DHA Ethyl Esters

A sample of the product of Example 3 was subjected to molecular distillation under the same pressure as in Example 3 but at a temperature of 50° C. The elimination of $C_{16}$ and $C_{18}$ acid ethyl esters in the distillate resulted in a product having a 40–50% total concentration of EPA/DHA ethyl esters.

EXAMPLE 5

50–60% Total Conc. EPA/DHA Ethyl Esters

The procedure of Example 4 was repeated on another sample of the product of Example 3 except that the molecular distillation temperature was 60°–70° C. Further removal of $C_{16}$ and $C_{18}$ acid ethyl esters resulted in a 50–60% total concentration of EPA/DHA ethyl esters.

EXAMPLE 6

60–70% Total Conc. EPA/DHA Ethyl Esters

The procedure of Example 5 was repeated except that the temperature was 70°–80° C. which resulted in a product having a 60–70% total concentration of EPA/DHA ethyl esters.

EXAMPLE 7

70–80% Total Conc. EPA/DHA Ethyl Esters

A sample of the product of Example 6 was subjected to molecular distillation at a pressure of $10^{-3}$ mm Hg and a temperature of 80°–90° C. A product having a 70–80% total concentration of EPA/DHA ethyl esters was obtained.

EXAMPLE 8

80–90% Total Conc. EPA/DHA Ethyl Esters

To a solution of 20 kg of urea in 120 liters of ethanol were added 15 liters of the product of Example 7 and the mixture shaken while heating under nitrogen. After cooling, the resultant precipitate was separated and the remaining solution vacuum concentrated to a small volume. After washing with water to remove all trace of urea, drying the organic solution and removing the solvent by vacuum distillation, the product was subjected to molecular distillation as in Example 3 but at an evaporator temperature of 70°–90° C. A product of 80–90% total concentration of EPA/DHA ethyl esters was obtained by virtue of $C_{16,18,20}$ acid ethyl esters being removed in the distillate.

EXAMPLE 9

90% Conc. DHA Ethyl Ester

A sample of the product of Example 8 is subjected to double molecular distillation under conditions as in Example 3 but at an evaporator temperature of 75°–95° C. The residue was 90% DHA ethyl ester while the distillate comprised EPA ethyl ester and minor amounts of other lower acid ethyl esters.

EXAMPLE 10

96% Conc. DHA Ethyl Ester

A sample of the product of Example 9 was subjected to molecular distillation under the same conditions as used in Example 9. The residue was 96% DHA ethyl ester while the distillate was essentially EPA ethyl ester together with minor amounts of other lower acid ethyl esters.

We claim:

1. A process for extracting an odor-free mixture of eicosapentaneoic acid (EPA) and docosahexanoic acid (DHA) ethyl esters from crude fish oil said odor-free mixture having a total EPA-DHA ethyl ester content of at least 65% and a DPA ethyl ester/EPA ethyl ester ratio of at least 3:2, which consists essentially of subjecting said crude fish oil to transesterification by diluting the latter with ethanol and refluxing in the presene of a catalytic amount of sulfuric acid; extracting the transesterification reaction product and subjecting said product to silica gel chromatography followed by molecular distillation at a pressure of about $10^{-3}$ mm Hg and at a temperature of about 65°–70° C.

2. A process according to claim 1 for producing a mixture having a DHA ethyl ester content of 85–95% which consists in dissolving the silica gel chromatographed reaction product in acetone with cooling to about −40° C., separating the resultant residue and subjecting it to two step molecular distribution in which the two step temperatures are 80°–100° C. and 105°–125° C., respectively.

* * * * *